US012782331B2

(12) United States Patent
Chou et al.

(10) Patent No.: US 12,782,331 B2
(45) **Date of Patent: *Nov. 3, 2026**

(54) SYSTEM AND METHOD FOR IN-LINE MONITORING OF AIRBORNE CONTAMINATION AND PROCESS HEALTH

(71) Applicant: Tricorntech Corporation, New Taipei City (TW)

(72) Inventors: Tsung-Kuan A. Chou, San Jose, CA (US); Pei-Wen Chung, Taipei City (TW); Li-Peng Wang, Taipei City (TW)

(73) Assignee: TRICORNTECH CORPORATION, New Taipei City (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/158,009

(22) Filed: Jan. 26, 2021

(65) Prior Publication Data

US 2021/0148876 A1 May 20, 2021

Related U.S. Application Data

(63) Continuation of application No. 15/496,931, filed on Apr. 25, 2017, now Pat. No. 10,948,470.

(Continued)

(51) Int. Cl.

| | |
|---|---|
| ***G01N 33/00*** | (2006.01) |
| ***G01N 15/00*** | (2024.01) |
| ***G01N 15/06*** | (2024.01) |

(52) U.S. Cl.

CPC ......... *G01N 33/0047* (2013.01); *G01N 15/06* (2013.01); *G01N 33/0044* (2013.01); *G01N 2015/0046* (2013.01)

(58) Field of Classification Search

CPC ............... G01N 33/0047; G01N 15/06; G01N 33/0044; G01N 2015/0046; G01N 33/0006; G01N 33/0022; G01N 33/0075

(Continued)

(56) References Cited

U.S. PATENT DOCUMENTS

| | | | | |
|---|---|---|---|---|
| 4,090,392 A * | 5/1978 | Smith | G01N 1/26 | 73/863.33 |
| 4,094,187 A * | 6/1978 | Navarre, Jr. | G01N 33/0006 | 73/864.34 |

(Continued)

FOREIGN PATENT DOCUMENTS

| | | |
|---|---|---|
| CN | 104299353 A | 1/2015 |
| CN | 104793002 A | 7/2015 |

(Continued)

OTHER PUBLICATIONS

Chinese office action and Search Report on the Patentability of Application No. 201780026637.X, Mailed on Sep. 9, 2020, 22 pages.

(Continued)

*Primary Examiner* — Marrit Eyassu
(74) *Attorney, Agent, or Firm* — WOMBLE BOND DICKINSON (US) LLP

(57) ABSTRACT

The disclosure describes embodiments of an airborne molecular contamination (AMC) monitoring apparatus. The AMC apparatus includes a manifold having a plurality of inlets and one or more outlets. A sampling tube bus fluidly is coupled to the manifold, the sampling tube bus comprising a plurality of individual sampling tubes, each individual sampling tube being fluidly coupled to one of the plurality of inlets. One or more analyzers are each fluidly coupled to one of the one or more outlets of the manifold to analyze fluid drawn into the manifold through one or more of the plurality of individual sampling tubes. A control and com- (Continued)

munication system coupled to the one or more analyzers. Other embodiments are described and claimed.

20 Claims, 12 Drawing Sheets

Related U.S. Application Data

(60) Provisional application No. 62/329,791, filed on Apr. 29, 2016.

(58) Field of Classification Search
USPC .......................................................... 73/28.01
See application file for complete search history.

(56) References Cited

U.S. PATENT DOCUMENTS

| | | | | | |
|---|---|---|---|---|---|
| 4,147,893 | A | | 4/1979 | Matson | |
| 4,705,669 | A | * | 11/1987 | Tsuji | G01N 33/0031 436/52 |
| 5,411,358 | A | | 5/1995 | Garric | |
| 5,804,695 | A | * | 9/1998 | Dageforde | G01N 33/0031 73/1.07 |
| 6,096,267 | A | * | 8/2000 | Kishkovich | G03F 7/70525 422/62 |
| 6,241,950 | B1 | | 6/2001 | Veelenturf | |
| 6,285,291 | B1 | * | 9/2001 | Knox | G08B 17/10 340/634 |
| 6,514,721 | B2 | * | 2/2003 | Spurrell | G01N 1/2205 435/31 |
| 6,615,679 | B1 | | 9/2003 | Knollenberg | |
| 8,147,302 | B2 | * | 4/2012 | Desrochers | F24F 11/46 702/50 |
| 8,196,479 | B2 | | 6/2012 | Ludwick | |
| 10,139,383 | B2 | | 11/2018 | Chou et al. | |
| 2002/0090735 | A1 | | 7/2002 | Kishkovich | |
| 2002/0174709 | A1 | * | 11/2002 | Kim | G01N 1/2273 73/31.01 |
| 2003/0041969 | A1 | * | 3/2003 | Schneider | G01N 15/06 156/345.24 |
| 2005/0120775 | A1 | | 6/2005 | Grayfer et al. | |
| 2006/0060004 | A1 | | 3/2006 | Desrochers et al. | |
| 2006/0108221 | A1 | * | 5/2006 | Goodwin | G01N 33/0009 204/424 |
| 2007/0107594 | A1 | * | 5/2007 | Piccinini | G01N 1/22 95/52 |
| 2007/0137283 | A1 | * | 6/2007 | Giandomenico | G01N 1/16 73/28.01 |
| 2010/0050742 | A1 | | 3/2010 | Northrup | |
| 2011/0088490 | A1 | * | 4/2011 | Ludwick | G01N 1/2273 73/863.31 |
| 2011/0136279 | A1 | | 6/2011 | Rho | |
| 2012/0241601 | A1 | | 9/2012 | Kaufman | |
| 2013/0047704 | A1 | | 2/2013 | Bae et al. | |
| 2014/0095083 | A1 | | 4/2014 | Chuang | |
| 2014/0238107 | A1 | * | 8/2014 | Chou | G01N 1/26 73/23.36 |
| 2015/0022363 | A1 | * | 1/2015 | Lang | G08B 17/10 340/628 |
| 2015/0234378 | A1 | | 8/2015 | Fosnight | |
| 2016/0061709 | A1 | | 3/2016 | Kaufman | |
| 2016/0223437 | A1 | * | 8/2016 | Ajay | G01N 1/26 |
| 2016/0282235 | A1 | | 9/2016 | Yoo | |
| 2018/0214050 | A1 | * | 8/2018 | Purves | G01N 33/004 |

FOREIGN PATENT DOCUMENTS

| | | | | | |
|---|---|---|---|---|---|
| CN | 105247363 | A | | 1/2016 | |
| CN | 105659067 | A | | 6/2016 | |
| JP | 58-003092 | A | | 1/1983 | |
| JP | 60-200145 | A | | 10/1985 | |
| JP | 06317508 | A | * | 11/1994 | |
| JP | 10-274644 | A | | 10/1998 | |
| JP | 11-125613 | A | | 5/1999 | |
| JP | 11-218512 | A | | 8/1999 | |
| JP | 11-281539 | A | | 10/1999 | |
| JP | 2003-051432 | A | | 2/2003 | |
| JP | 2006-133200 | A | | 5/2006 | |
| JP | 2006-261678 | A | | 9/2006 | |
| JP | 2008-545990 | A | | 12/2008 | |
| JP | 2013-137219 | A | | 7/2013 | |
| JP | 2014-199230 | A | | 10/2014 | |
| KR | 10-2000-0075832 | A | | 12/2000 | |
| KR | 10-1250249 | B1 | | 4/2013 | |
| KR | 101491234 | B1 | | 2/2015 | |
| KR | 10-2015-0143453 | A | | 12/2015 | |
| PL | 202007 | B1 | * | 5/2009 | |
| TW | 201250053 | A | | 12/2012 | |
| TW | 201502508 | A | | 1/2015 | |
| TW | 201527755 | A | | 7/2015 | |
| TW | 201530112 | A | * | 8/2015 | G01F 1/66 |
| WO | 98/38508 | A1 | | 9/1998 | |
| WO | 2006/017143 | A1 | | 2/2006 | |
| WO | 2012/042035 | A1 | | 4/2012 | |
| WO | 2013/047704 | A1 | | 4/2013 | |

OTHER PUBLICATIONS

Final Office Action received for U.S. Appl. No. 15/496,931, mailed on Aug. 29, 2019, 19 pages.
Final Office Action received for U.S. Appl. No. 15/496,931, mailed on Jul. 21, 2020, 18 pages.
International Preliminary Report on Patentability received for PCT Patent Application No. PCT/US2017/029674, mailed on Nov. 8, 2018, 9 pages.
International Search Report and Written Opinion received for PCT Patent Application No. PCT/US2017/029674, mailed on Jul. 11, 2017, 10 pages.
Non-Final Office Action received for U.S. Appl. No. 15/496,931, mailed on Dec. 11, 2019, 16 pages.
Non-Final Office Action received for U.S. Appl. No. 15/496,931, mailed on Feb. 25, 2019, 15 pages.
Notice of Allowance received for U.S. Appl. No. 15/496,931, mailed on Feb. 18, 2021, 2 pages.
Notice of Allowance received for U.S. Appl. No. 15/496,931, mailed on Oct. 29, 2020, 8 pages.
Office Action for Taiwan Patent Application No. 106114334 mailed Aug. 2, 2018, 11 pages.
Search Report and Written Opinion received for Singapore Patent Application No. 11201809349S, mailed on Jan. 28, 2020, 9 pages.
Office Action received for Taiwanese Patent Application No. 108114373, mailed on Jan. 5, 2022, 10 pages (4 pages of English Translation and 6 pages of Office Action).
Office Action received for Chinese Patent Application No. 201780026637.X, mailed on Apr. 30, 2021, 12 pages (5 pages of English Translation and 7 pages of Office Action).
Office Action received for Japanese Patent Application No. 2018-556922, mailed on Mar. 15, 2021, 8 pages (3 pages of English Translation and 5 pages of Office Action).
Office Action received for Korean Patent Application No. 10-2018-7034321, mailed on Jun. 4, 2021, 9 pages (4 pages of English Translation and 5 pages of Office Action).
Office Action received for SG Patent Application No. 11201809349S, mailed on Jun. 14, 2021, 7 pages.
Office Action received for Taiwanese Patent Application No. 108114373, mailed on Mar. 22, 2021, 10 pages (4 pages of English Translation and 6 pages of Office Action).
Decision to Grant received for Japanese Patent Application No. 2018-556922, mailed on Jul. 5, 2021, 5 pages (2 pages of English Translation and 3 pages of Original Document).
First Office Action received for Chinese Patent Application No. 201780026637.X, mailed on Sep. 2, 2020, 21 pages (11 pages of English Translation and 10 pages of Original Document).
Notice of Allowance received for Chinese Patent Application No. 201780026637.X, mailed on Sep. 1, 2021, 3 pages (2 pages of English Translation and 1 page of Original Document).

(56) References Cited

OTHER PUBLICATIONS

Notice of Allowance received for Korean Patent Application No. 10-2018-7034321, mailed on Dec. 9, 2021, 3 pages (1 page of English Translation and 2 pages of Original Document).
Notice of Allowance received for Korean Patent Application No. 10-2022-7008056, mailed on Jun. 22, 2023, 6 pages (3 pages of English Translation and 3 pages of Original Document).
Notice of Allowance received for Singapore Patent Application No. 11201809349S, mailed on Aug. 12, 2022, 5 pages.
Notice of Allowance received for Taiwan Patent Application No. 108114373, mailed on Sep. 8, 2022, 3 pages Original Document Only.
Office Action received for Japanese Patent Application No. 2021-128050, mailed on Apr. 20, 2023, 6 pages (3 pages of English Translation and 3 pages of Original Document).
Office Action received for Japanese Patent Application No. 2021-128050, mailed on Aug. 24, 2022, 12 pages (7 pages of English Translation and 5 pages of Original Document).
Office Action received for Korean Patent Application No. 10-2022-7008056, mailed on Dec. 26, 2022, 6 pages (3 pages of English Translation and 3 pages of Original Document).
Office Action received for Korean Patent Application No. 10-2022-7008056, mailed on Jun. 15, 2022, 5 pages (2 pages of English Translation and 3 pages of Original Document).
Office Action received for Chinese Patent Application No. 202111326570.6, mailed on Apr. 22, 2023, 8 pages (2 pages of English Translation and 6 pages of Original Document).
Office Action for Taiwan Patent Application No. 111147537, Sep. 3, 2025, 6 pages. [Includes English translation].
Office Action for Korean Patent Application No. 10-2023-7031718, Oct. 31, 2024, 6 pages. [Includes English translation].
Written Opinion for Korean Patent Application No. 10-2023-7031718, Mar. 31, 2025, 14 pages. [Includes English translation].
Notice of Allowance for Korean Patent Application No. 10-2023-7031718, Oct. 23, 2025, 8 pages. [Includes English translation].
Notification of Grant for Chinese Application No. 202111326570, Jan. 30, 2024, 5 pages. [Includes English translation].

* cited by examiner

SYSTEM AND METHOD FOR IN-LINE MONITORING OF AIRBORNE CONTAMINATION AND PROCESS HEALTH

CROSS-REFERENCE TO RELATED APPLICATIONS

This application is a continuation under 35 U.S.C. § 120 of U.S. application Ser. No. 15/496,931, filed 25 Apr. 2017, which in turn claims priority under 35 U.S.C. § 119(e) to U.S. Provisional App. No. 62/329,791, filed 29 Apr. 2016. Both priority applications are hereby incorporated by reference in their entirety.

TECHNICAL FIELD

The disclosed embodiments relate generally to air-borne contamination monitoring and in particular, but not exclusively, to a system and method for in-line monitoring of airborne contamination and process health.

BACKGROUND

Air quality and airborne molecular contamination (AMC) have been gaining increasing attention in the semiconductor, memory, and other similar high-tech industries (e.g., display) as their processes advance. In these industries, among others, AMC has been identified as major contribution to fabrication failure rate, and the effects of AMC on manufacturing process yield just get worse as the fabrication technology becomes capable of smaller component sizes. Prolonged exposure to AMC has also been identified as a possible risk to human health.

Manufacturers have been putting significant efforts into on-site continuous monitoring and into controlling facility ambient cleanliness using on-site or off-line AMC sensing equipment. Detailed studies and on-going improvements have been implemented to identify contamination sources and preventive procedures to reduce AMC in a facility's ambient air.

But although significant efforts have been made to control facility ambient air quality, the cleanliness inside manufacturing equipment such as process equipment modules and movable carriers (e.g., Front Opening Unified Pods (FOUPs) used as substrate/wafer transport containers in the semiconductor industry) are not well-studied. Specific process equipment modules or movable carriers can also contribute to AMC, but in most situations the process equipment modules and substrates have their own enclosed micro-environments, meaning that on-site facility ambient monitoring cannot capture AMC-related problems associated with process equipment modules or movable carriers. Furthermore, when one process equipment module or one movable carrier is contaminated, AMC cross-contamination can occur over a fabrication line, with the movable carrier serving as an AMC carrier that spreads contamination to various locations. As a result, it becomes extremely difficult to trace the source of contamination, even if AMC is later found in one movable carrier or process equipment module.

BRIEF DESCRIPTION OF THE DRAWINGS

Non-limiting and non-exhaustive embodiments are described with reference to the following figures, in which like reference numerals refer to like parts throughout the various views unless otherwise specified.

DETAILED DESCRIPTION OF THE ILLUSTRATED EMBODIMENTS

Embodiments are described of a system and method for in-line monitoring of airborne contamination and process health. Specific details are described to provide an understanding of the embodiments, but one skilled in the relevant art will recognize that the invention can be practiced without one or more of the described details or with other methods, components, materials, etc. In some instances, well-known structures, materials, connections, or operations are not shown or described in detail but are nonetheless encompassed within the scope of the invention.

Reference throughout this specification to "one embodiment" or "an embodiment" means that a described feature, structure, or characteristic can be included in at least one described embodiment, so that appearances of "in one embodiment" or "in an embodiment" do not necessarily refer to the same embodiment. Furthermore, the particular features, structures, or characteristics may be combined in any suitable manner in one or more embodiments.

Figure 1A:
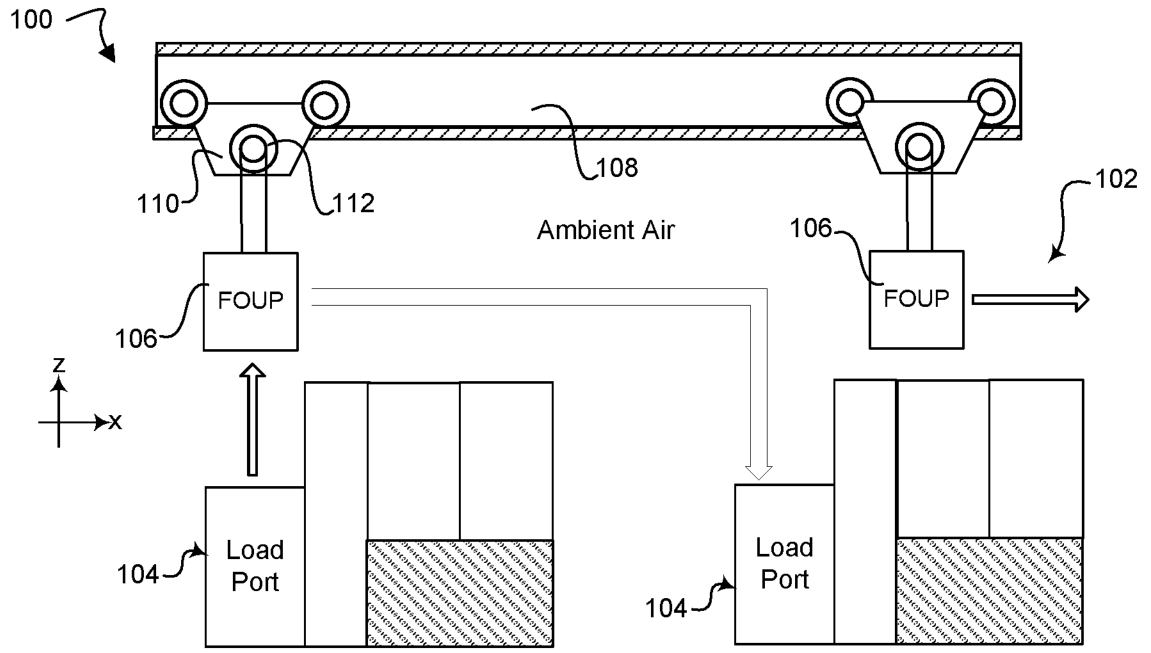
FIGS. 1A-1B are drawings of an embodiment of a manufacturing process used for semiconductor fabrication.
Figure 1B:
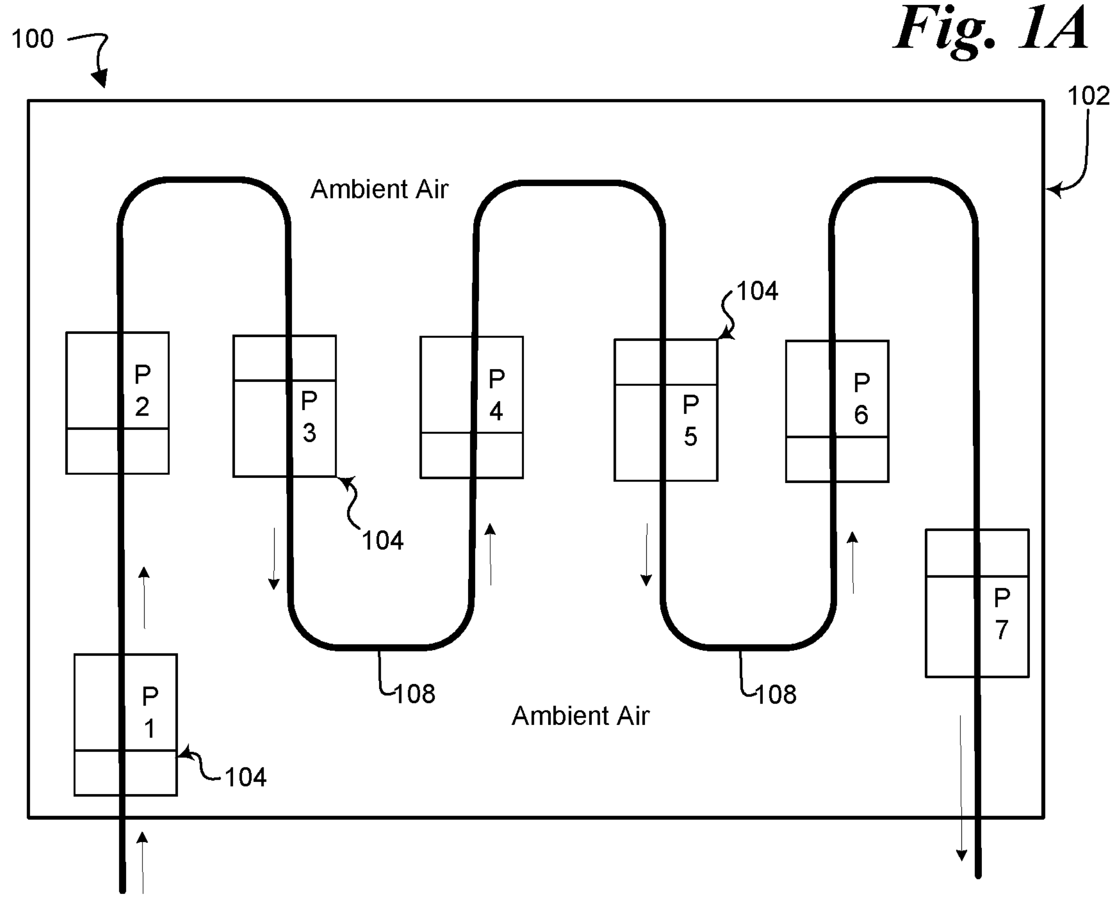

FIGS. 1A-1B illustrate an embodiment of a manufacturing line 100. Manufacturing line 100 can be used in semiconductor fabrication, for instance, but in other embodiments could be used for other purposes and with different equipment than shown.

Manufacturing line 100 is positioned in an enclosure 102, which can be a building, a room or bay within a building, or some other type of enclosure. One or more process equipment modules 104 are positioned within enclosure 102. Each process equipment module 104 includes a load port and can include one or more chambers, each of which performs different functions related to the manufacturing steps carried out by that particular process equipment module.

Manufacturing processes generally involve many steps, and each process equipment module performs only some of the steps in the overall manufacturing process. As a result, the items being manufactured on manufacturing line 100—semiconductor wafers with processors, memories, MEMS chips, optical chips, etc., in a semiconductor manufacturing facility—must be moved from one process equipment module to another until all the steps in the process are performed. Moving the items being manufactured is accomplished using movable carriers 106 that carry the items being manufactured inside, often in a sealed micro environment. In a semiconductor facility embodiment such as the one shown, movable carriers 106 are called Front-Opening Unified Pods (FOUPs), wafer containers, or substrate containers, because they are used to transport semiconductor wafers. But in other embodiments other types of movable carrier can be used.

A transport system carries each movable carrier 106 from the load port of one process equipment module 104 to the load port of another, so that different steps can be performed on the items being manufactured that are carried inside the movable carrier. In the illustrated embodiment, the transport system is an overhead track-and-hoist system. Wheeled and motorized carriages 110 run along a track 108. A hoist 112 is mounted to each wheeled carriage 110 to lift movable carriers 106 in the z direction and also potentially move them in the y direction (i.e., into and out of the page) so that movable carriers 106 can be placed on load ports that can accommodate multiple carriers.

As best seen in FIG. 1B, track 108 winds through facility 102 to transport the movable carriers 106—and hence the items being manufactured, which are carried inside the movable carriers—to multiple process equipment modules; the illustrated embodiment has seven processing equipment modules P1-P7, but other embodiments can have a different number. After the items being manufactured move through all the process equipment modules 104 in a particular enclosure 102, the transport system exits enclosure 102 with the movable carrier.

Significant effort and studies have been done to control the facility ambient air quality in enclosure 102, but the cleanliness of the environment inside process equipment modules 104 and inside movable carriers 106 are not well-studied. In addition to the facility ambient contaminants—that is, contaminants that come from the facility's overall air handling systems such as ventilation and air conditioning—process equipment modules 104 or movable carriers/FOUPs 106 can contribute Airborne Molecular Contamination (AMC). Because the process equipment modules 104 and movable carriers 106 include closed chambers with their own internal micro-environments, on-site overall facility ambient monitoring cannot capture AMC problems associated with process equipment modules or movable carriers. For instance, when one process equipment module or one movable carrier is contaminated, cross-contamination can spread AMC over the fabrication line, with the movable carrier 106 serving as an AMC carrier that transmits AMC to various locations. But with existing overall facility ambient monitoring it is extremely difficult to trace the source of contamination even if AMC is later found in one movable carrier or process equipment module.

An alternative method is to install an on-site movable-carrier-only AMC monitoring system. In such systems, when wafers are finished in one process equipment module and stored in a movable carrier for transport to another, the movable carrier is detoured from its normal process sequence and sent to the on-site AMC movable carrier monitoring system for analysis on the air inside. But although such an AMC monitoring system can be an on-site monitoring tool, it is actually an off-process monitoring method because the movable carrier no longer follows the regular process sequence. And since the movable carrier must be detoured from normal fabrication to be analyzed, the approach introduces additional uncertainties due to interference in the normal process sequence. Moreover, in such an approach, the on-site movable-carrier-only AMC monitoring system has limited capacity and can only test a limited number of movable carriers (also, this way it will not significantly impact the process throughput). And even if the monitoring system can increase its screening capacity, the need to detour movable carriers still adds extra process sequence to the fabrication, which in turn slows down process throughput. Therefore, such an approach is limited only to screening movable carriers. It does not serve the purpose of in-line AMC monitoring on movable carriers and process equipment modules.

Figure 2:
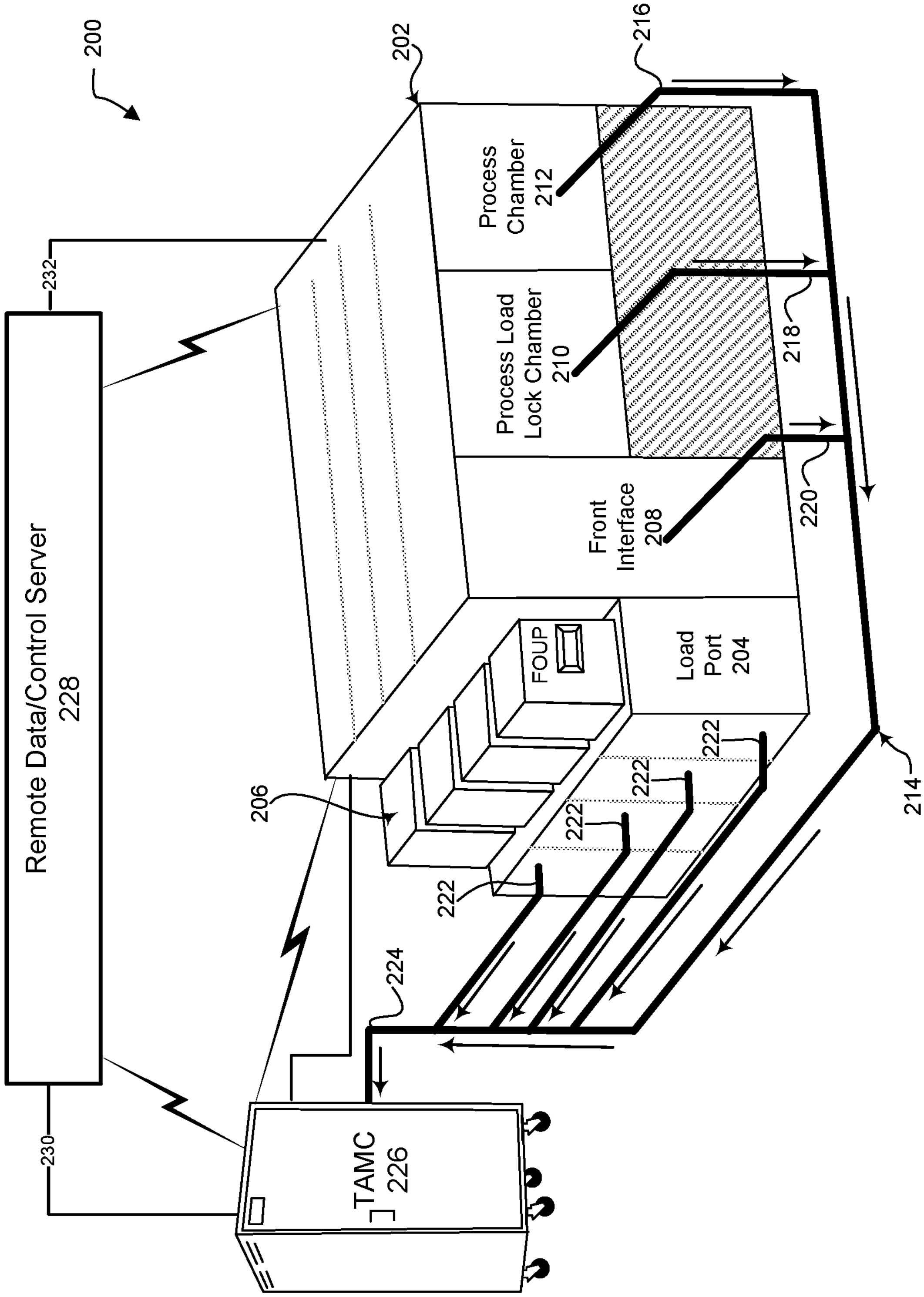
FIG. 2 is a drawing illustrating an embodiment of an in-line monitoring application of a Total Airborne Molecular Contamination (TAMC) apparatus in semiconductor fabrication.

FIG. 2 illustrates an embodiment of an in-line monitoring system 200 using a Total Airborne Molecular Contamination (TAMC) apparatus 226 fluidly coupled to a process equipment module 202. In the illustrated embodiment, process equipment module 202 includes a load port 204 on which one or more movable carriers 206 (FOUPs in this embodiment) can be loaded; the illustrated embodiment shows a load port capable of receiving four movable carriers, but in other embodiments the load port can accommodate a different number of movable carriers than shown. Process equipment module 202 includes three chambers in addition to load port 204: a front interface 208 is next to load port 204, a process load lock chamber 210 is next to front interface 208 and, finally, a process chamber 212, where the relevant manufacturing steps are performed on the items being manufactured, is next to load lock chamber 210.

Individual sampling tubes are fluidly coupled to each chamber within process equipment module 202. As used herein, when components are "fluidly coupled" it means that they are coupled in such a way that fluid can flow from one to or through the other. Individual sampling tube 216 is fluidly coupled to process chamber 212, individual sampling tube 218 is fluidly coupled to load lock chamber 210, and individual sampling tube 220 is fluidly coupled front interface 208. Individual sampling tubes 216, 218, and 220 form a sampling tube bus 214. Individual sampling tubes 222 are fluidly coupled to load port 204—or, more specifically, to the components within load port 204 that will fluidly couple to the interiors of movable carriers 206. In the illustrated embodiment there are four individual sampling tubes 222 because load port 204 can accommodate four movable carriers, but in other embodiments the number of individual sampling tubes can match the number of movable carriers that the load port can accommodate. Sampling tube bus 214 and individual sampling tubes 222 then form a further sampling tube bus 224 that is fluidly coupled to TAMC 226.

TAMC 226 is communicatively coupled, by wire or wirelessly, to a remote data/control server 228. Process equipment module 202 is also communicatively coupled, by wire or wirelessly, to remote data control server 228 and/or directly to TAMC 226. Remote data control server 228 can also be communicatively coupled, by wire or wirelessly, directly to process equipment module 202.

In operation of in-line monitoring system 200, the movable carriers/FOUPs are transferred to the load port, such that their bottom air inlets and outlets fluidly coupled to mating inlets/outlets in the load ports that will purge either $N_2$ or clean air (XCDA) to flush air/AMC out from the interior of movable carriers 206 to an exhaust outlet under the load port. In one embodiment, individual sampling tubes 222 can be connected to the exhaust of the load port purging system, where they can then collect, analyze, and report the purged air cleanliness from each movable carrier 206. The exhaust air cleanliness represents the contamination level of the micro-environment in each movable carrier, which can be linked to the cleanliness of their previous process at another location. After the short purge process, the movable carrier's front door is opened and the wafers inside are transferred into the other chambers of the process equipment module—front interface 208, load lock 210, and process chamber 212, in that sequence—for the required fabrication steps.

In addition to monitoring AMC inside movable carriers 206, system 200 can, additionally or simultaneously, monitor AMC in the interiors of front interface (FI) chamber 208, the load lock chamber 210, or the process chamber 212, which can be sampled and analyzed by the TAMC apparatus 226 to understand the cleanliness of each chamber. While waiting for each wafer (typically 25 wafers in a FOUP) to be processed in the chambers of process equipment module 202, TAMC apparatus 226 can continue sampling and analysis of air collected from each channel (i.e., each individual sampling tube) to record changes in AMC levels. Such an AMC monitoring process provides in-line real time AMC results for specific process steps and locations, but without altering existing fabrication procedures because the system can directly collect air sample from the specific target via the corresponding tube channel in-line without interfering the normal manufacturing process sequence. With system 200 there is no need to pull the movable carriers/FOUPs 206 from their normal process for AMC analysis.

One or both of TAMC 226 and process equipment module 202 can communicate wired or wirelessly with a remote data/control server 228, so that they can receive commands on when and which channel (i.e., individual sampling tube) to sample and analyze. Meanwhile, TAMC 226 can report test results back to remote server 228 as feedback for fabrication process control, which server 228 can then communicate to the process equipment module 202, by wire or wirelessly, to cause adjustments such as modification of the fabrication recipe. In another embodiment, TAMC apparatus 226 can be programmed to directly communicate with the process equipment, by wire or wirelessly, to control the fabrication process based on the in-line AMC results measured by the TAMC apparatus. Sampling and analysis at the load port 204, front interface 208, load lock 210, or process chamber 212 can be in time sequence or in parallel, and can either be pre-programmed in the TAMC apparatus 226 or accomplished with commands sent from remote data/control server 228.

Figure 3A:
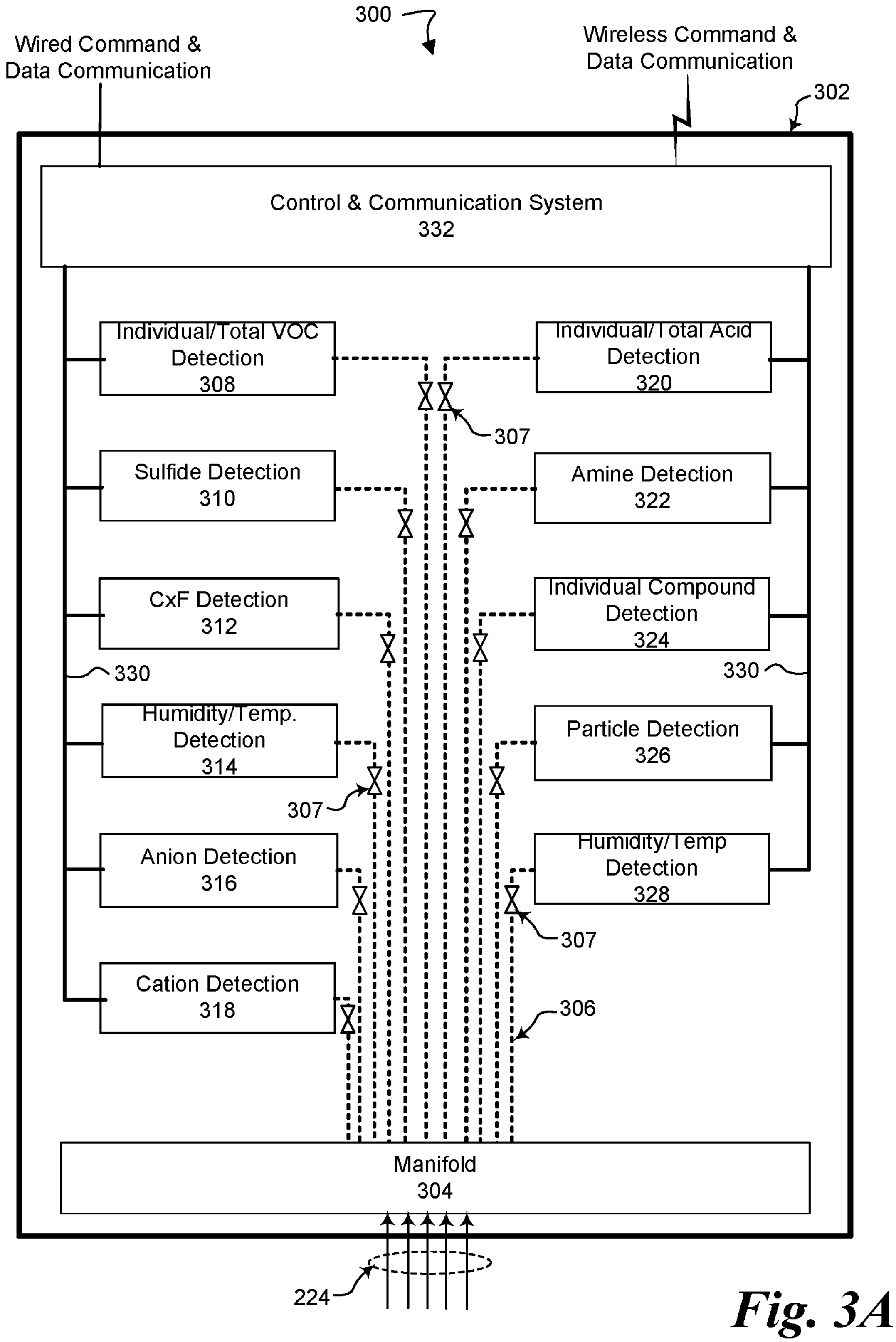
FIG. 3A is a block diagram of an embodiment of a TAMC apparatus.

FIGS. 3A-3D together illustrate embodiments of a TAMC apparatus 300 that can be used in an in-line monitoring system and method for airborne contamination and process health monitoring, such as shown in FIGS. 2 and 4-9. FIG. 3A is a block diagram of an embodiment of TAMC apparatus 300, which comprises a combination of several devices to collect, analyze, and report AMC detection results.

TAMC 300 is housed within a housing 302, which can be fixed or movable. For instance, housing 302 can be a fixed or movable cabinet, or in some embodiments it can be a movable carrier such as movable carriers 206 (see, e.g., FIG. 9). TAMC 300 includes a manifold 304 with inlets that are fluidly coupled to the individual sampling tubes from sampling tube bus 224 (see FIGS. 3B-3C). Manifold 304 also includes one or more outlets fluidly coupled to a variety of analyzers via tubes 306. Tubes 306 include valves 307 so that output from the manifold can be selectively directed to any analyzer or combination of analyzers. Tubes 306 are inert to all AMC compounds and do not attract AMC compounds either. They can be a passivated or coated metal tube, or an inert plastic tube (e.g., PFA or Teflon).

Analyzers 308-328 can include sensors or sensor arrays for their particular type of detection, but in some embodiments they can also include additional components including gas chromatographs, pre-concentrators, traps, filters, valves, and so forth. Various gas analyzers (VOCs, acids, bases, etc.), particle counter, humidity sensor, temperature sensor, ions analyzers can be used in different embodiments. Among others, and without being limited to the listed analyzers, embodiments of TAMC 300 can include one or more of the following types of analyzers:

- An analyzer to collect and analyze the concentrations of specific (individual) volatile organic compounds (VOCs), such as IPA and/or detect total concentration of VOCs.
- An analyzer to collect and analyze the concentrations of specific (individual) acid compounds (e.g., HF, $H_2SO_4$, HCL, etc.) and/or detect total concentration of acids.
- An analyzer to collect and analyze the concentrations of specific (individual) base compounds (e.g., $NH_4OH$, NaOH, etc.) and/or detect total concentration of bases.
- An analyzer to collect and analyze the concentrations of specific (individual) Sulfide compounds and/or detect total concentration of Sulfides.
- An analyzer to collect and analyze the concentrations of specific (individual) Amine compounds and/or detect total concentration of Amines.
- An analyzer that is connected to the manifold apparatus to detect air particle or aerosol counts.
- An analyzer to detect sample humidity.
- An analyzer to detect the sample temperature.
- An analyzer to detect fluoride compounds, such as chemical coolant agents (e.g., Carbon Fluoride compounds (CxF)) or dry etching chemicals (e.g., CxFy), and/or detect total concentration of chemical cooling agents such as Carbon Fluorides or total concentration of dry etching agents.
- An analyzer to collect and analyze the concentrations of specific (individual) Anions (negatively-charged ions), such as F—, Cl—, PO43-, NOx-, SO22-, and/or detect total concentration of Anions.
- An analyzer to collect and analyze the concentrations of specific (individual) Cations (positively-charged ions), such NH4+, and/or detect total concentration of Cations.
- An analyzer to collect and analyze the concentrations of specific (individual) Metal ions and/or detect total concentration of Metal Ions.
- An analyzer to collect and analyze the concentrations of specific (individual) silicon doping ions and/or detect total concentration of dopants.

Analyzers 308-328 are communicatively coupled to control and communication system 332, which integrates the operation of all the analyzers and apparatus included in the TAMC apparatus 300. Control and communication system 332 is used to receive, process, and/or interpret data received from analyzers 308-328, and each analyzer and its associated valve 307 can be controlled by the control and communication system for sample analysis. In one embodiment, the hardware of control and communication system 332 can be a general-purpose computer including a processor, memory, storage, and so on, together with software having instructions that cause the listed hardware to perform the required functions. In other embodiments, however, control and communication system 332 can be a special-purpose computer such as an application specific integrated circuit (ASIC), also with software having instructions that cause it to perform the required functions.

Control and communication system 332 can be communicatively coupled, by wire or wirelessly, to one or more process equipment modules, and/or to a remote data/control server (see, e.g., FIG. 2) that gathers data from each TAMC and that can control each TAMC and the process equipment to which it is coupled. The TAMC system can thus receive and transmit real-time test results update or receive operation commands from the server, such as the specific sampling channel (i.e., a specific individual sampling tube) on which to perform in-line AMC analysis.

As shown and discussed elsewhere (see FIGS. 2 and 4-9), one or more TAMCs 300 can be used to monitor multiple movable carriers/FOUPs, multiple chambers in of one or more process equipment modules, or combinations of the movable carriers and process equipment modules. Use of TAMC 300 provides a method of direct in-line monitoring without interfering with the normal manufacturing process.

Figure 3B:
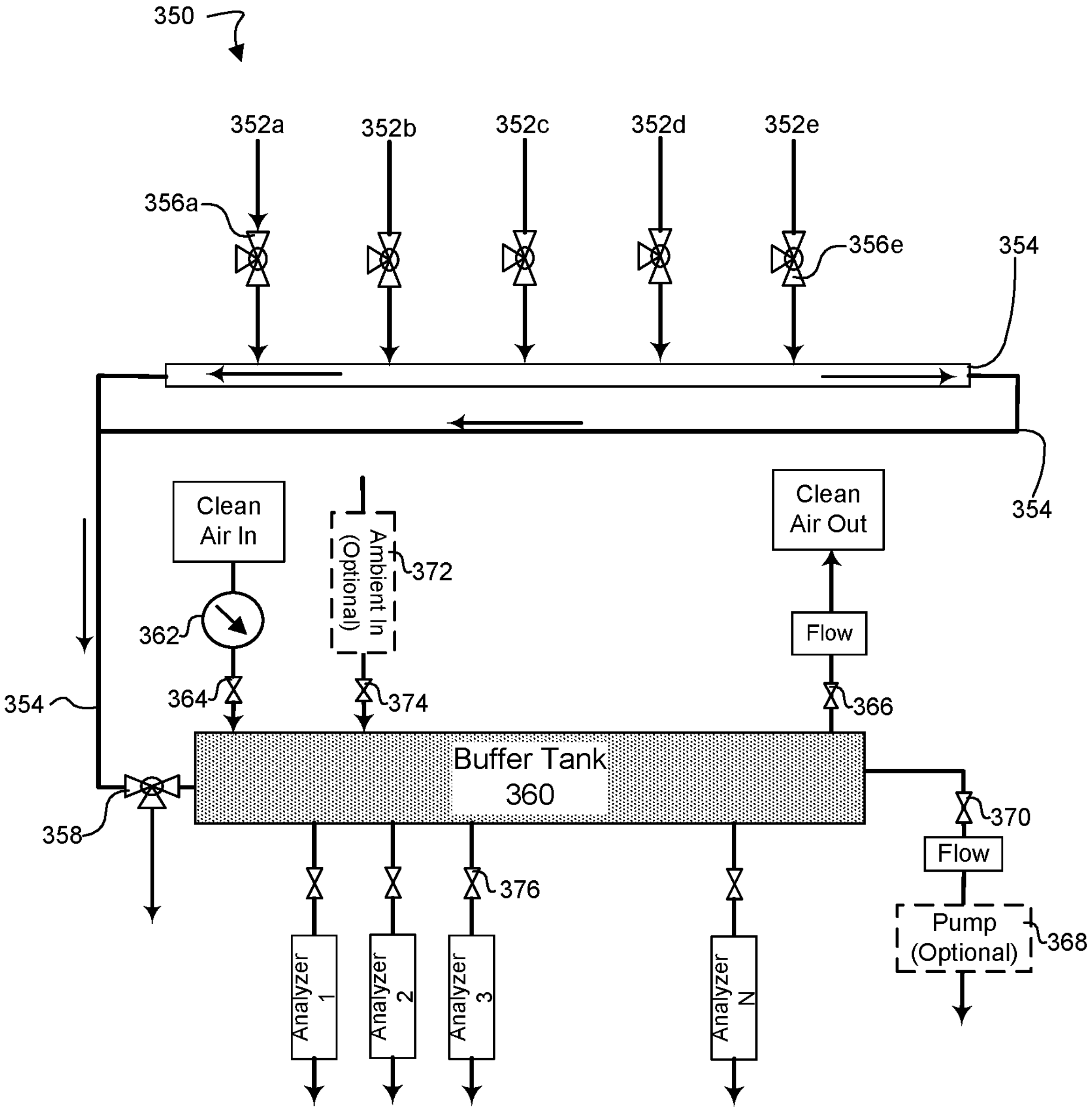
FIGS. 3B-3D are block diagrams of embodiments of manifolds that can be used in the embodiment of a TAMC apparatus shown in FIG. 3A.

FIG. 3B illustrates an embodiment of a manifold 350 that can be used in TAMC system 300. Manifold 350 includes one or more inlet tubes 354 fluidly coupled, via three-way valves 356, to individual sampling tubes 352. The illustrated embodiment has five individual sampling tubes 352*a*-352*e* with corresponding valves 356*a*-356*e*, but other embodiments can be configured with a different number of individual sampling tubes and a different number of valves, and not every sampling tube need have a valve.

In the illustrated embodiment, inlet tube 354 has a design that eliminates dead space that can trap contaminants in the inlet tube. Each three-way valve 356 has an additional port that can be used as a flush port for its individual sampling tube, but in other embodiments other types of valves can be used instead of three-way valves 356.

A buffer tank 360 is fluidly coupled to inlet tube 354 via a three-way valve 358. Buffer tank allows TAMC system 300 to collect a large volume of sample within a short period of time (e.g., 20 liters within 5 seconds). In some situations, the AMC contamination level may change after less than 10 seconds. Valves 358 and 270 (which can be three-way valves or switch valves) are placed at the inlet and outlet of buffer tank 360; these valves open when air sampling is needed and close when air sample is collected. Buffer tank 360 also allows collection of transient AMC from the outlet of specific location for the analyzers to measure the contamination level later on.

Buffer tank 360 has a clean air inlet fluidly coupled to its interior via pressure controller 362 and valve 364, as well as a clean air outlet fluidly coupled to the interior of the buffer tank 360 by valve 366. The clean air inlet and clean air outlet provide the ability to flush the interior of buffer tank 360 to clean any sample that remains inside the buffer tank or sampling tubes. Buffer tank 360 can also optionally have in ambient air inlet 372 coupled fluidly coupled to the interior of buffer tank 360 by valve 374.

An optional sampling pump 368 can be fluidly coupled to the interior of buffer tank 360 via valve 370. When present, sampling pump 368 can be used to draw samples received at inlet tube 354 into the intenor of buffer tank 360. Sampling pump 368 reduces pressure in buffer tank 360 to extract the air from the outlets of load port exhaust, FI, load lock, or process chamber. In embodiments where the outputs of the load port exhaust, FI chamber, load lock chamber, or process chamber, and hence individual sampling tubes 352, have positive pressure/flow, sampling pump 368 might not be required.

One or more analyzers, up to N analyzers, can be fluidly coupled to the outlet of buffer tank 360 via valves 376; these analyzers correspond to analyzers 308-328 shown in FIG. 3A. A non-exclusive list of the types of analyzers that can be used in different embodiments is provided above in connection with FIG. 3A.

Figure 3C:
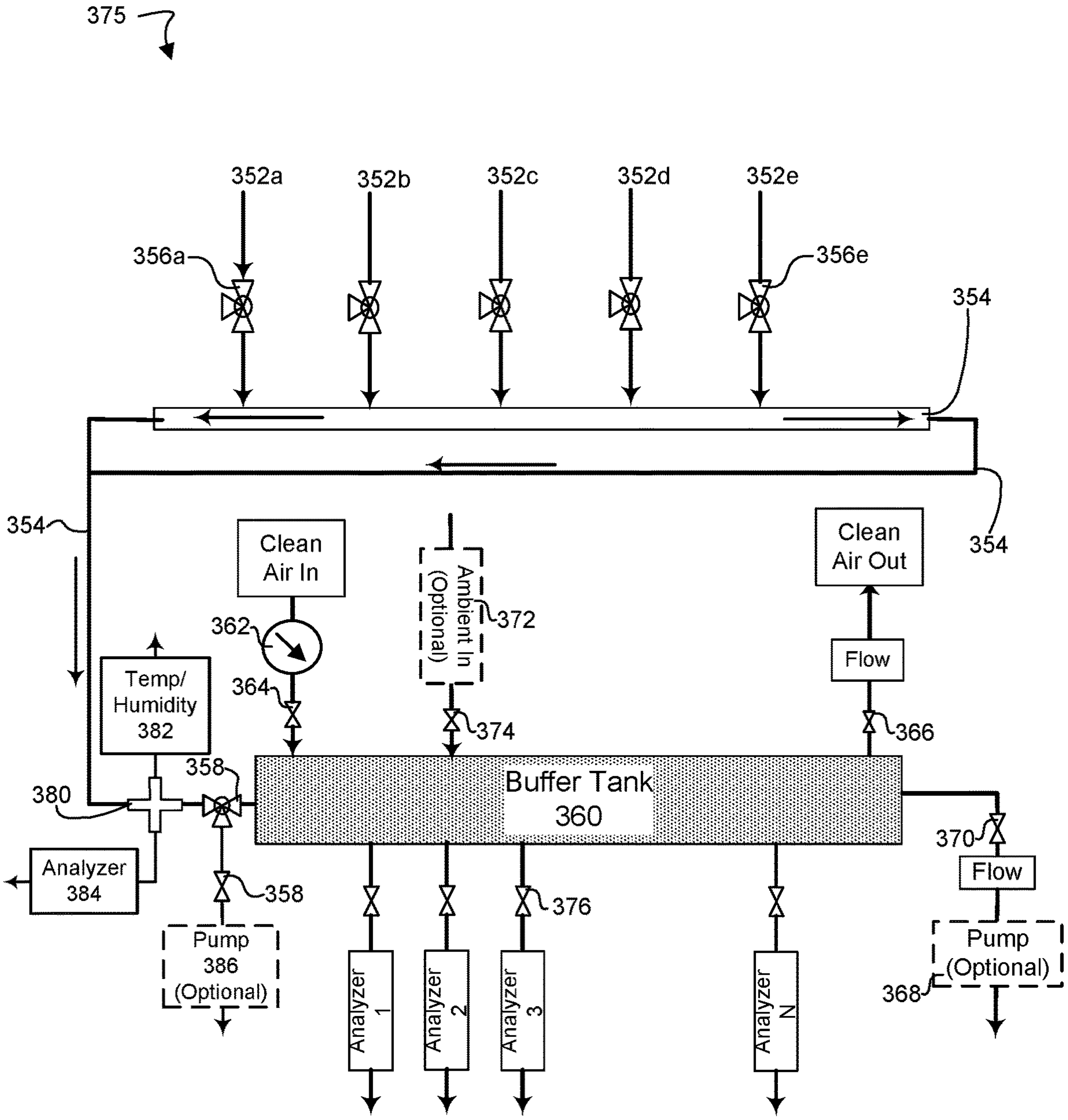

FIG. 3C illustrates an embodiment of a manifold 375 that can be used in TAMC 300. Manifold 375 is similar in most respects the manifold 350. The primary difference between manifolds 375 and 350 is that that in some instances it may be useful to analyze samples before they go into buffer tank 360. Some analyzers/sensors have fast sensing response or contain internal fast sampling modules which do not need to be connected to the buffer tank to share the collected sample. To accommodate that, manifold 375 has a diverter 380 fluidly coupled in tube 354 upstream of three-way valve 358. Diverter 380 is in turn fluidly coupled to one or more analyzers such as a temperature/humidity analyzer 382 or some other type of analyzer 384. In such an embodiment, the analyzer/sensor does not consume the sample collected in buffer tank 360.

Figure 3D:
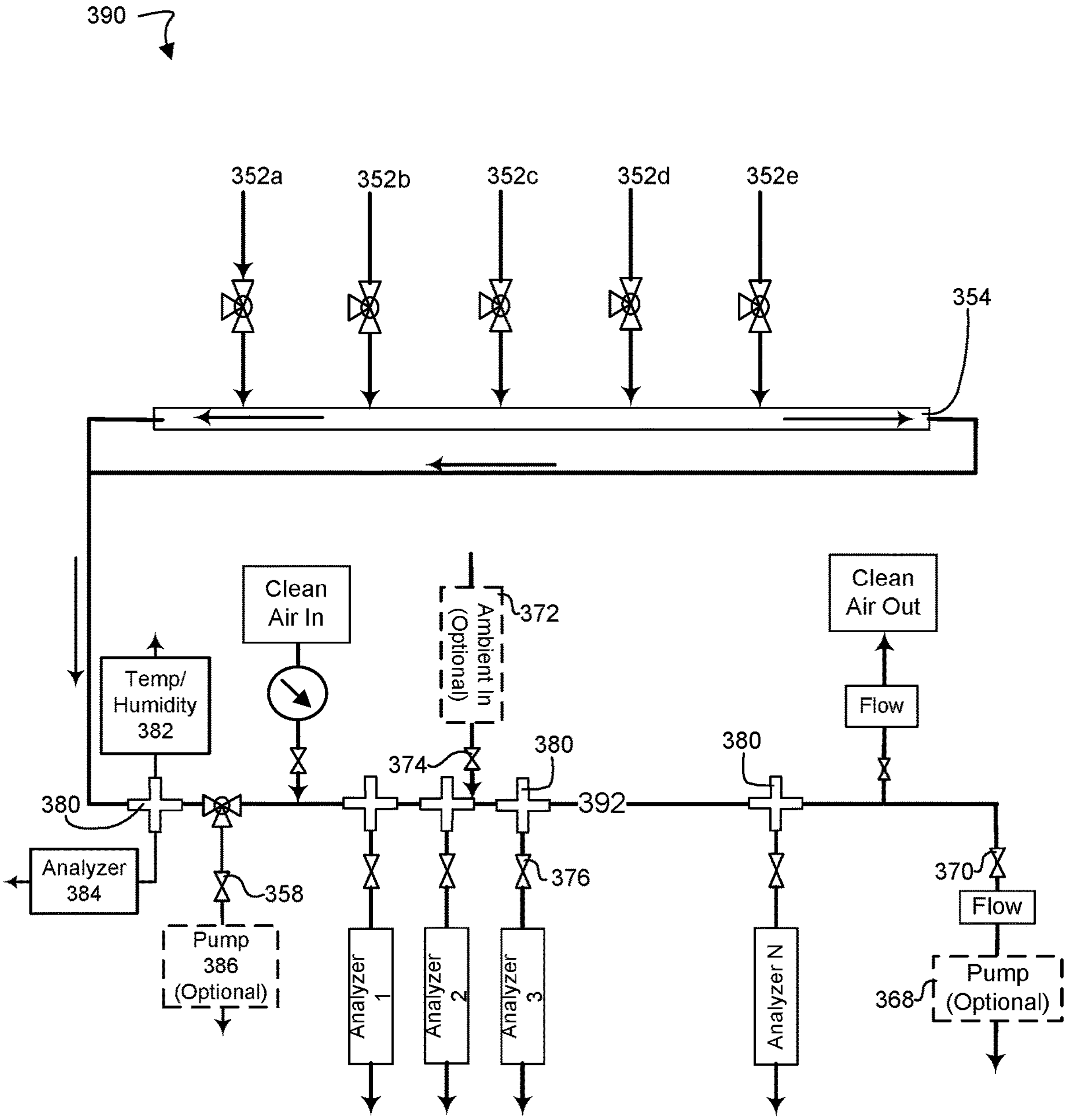

FIG. 3D illustrates another embodiment of a manifold 390. Manifold 390 is similar in most respects to manifolds 350 and 370. The primary difference is that manifold 390 does not include buffer tank 360. In embodiments where a buffer tank is not needed to collect and preserve large sample volumes, buffer tank 360 can be replaced by a tube 392 with fluid couplings to individual analyzers. For instance, in one embodiment tube 392 could be coupled to the N analyzers using multiple diverters (e.g., like diverter 380 in one embodiment) connected in series to tube 392 to divert sample fluid to one or more of the N individual analyzers.

Figure 4:
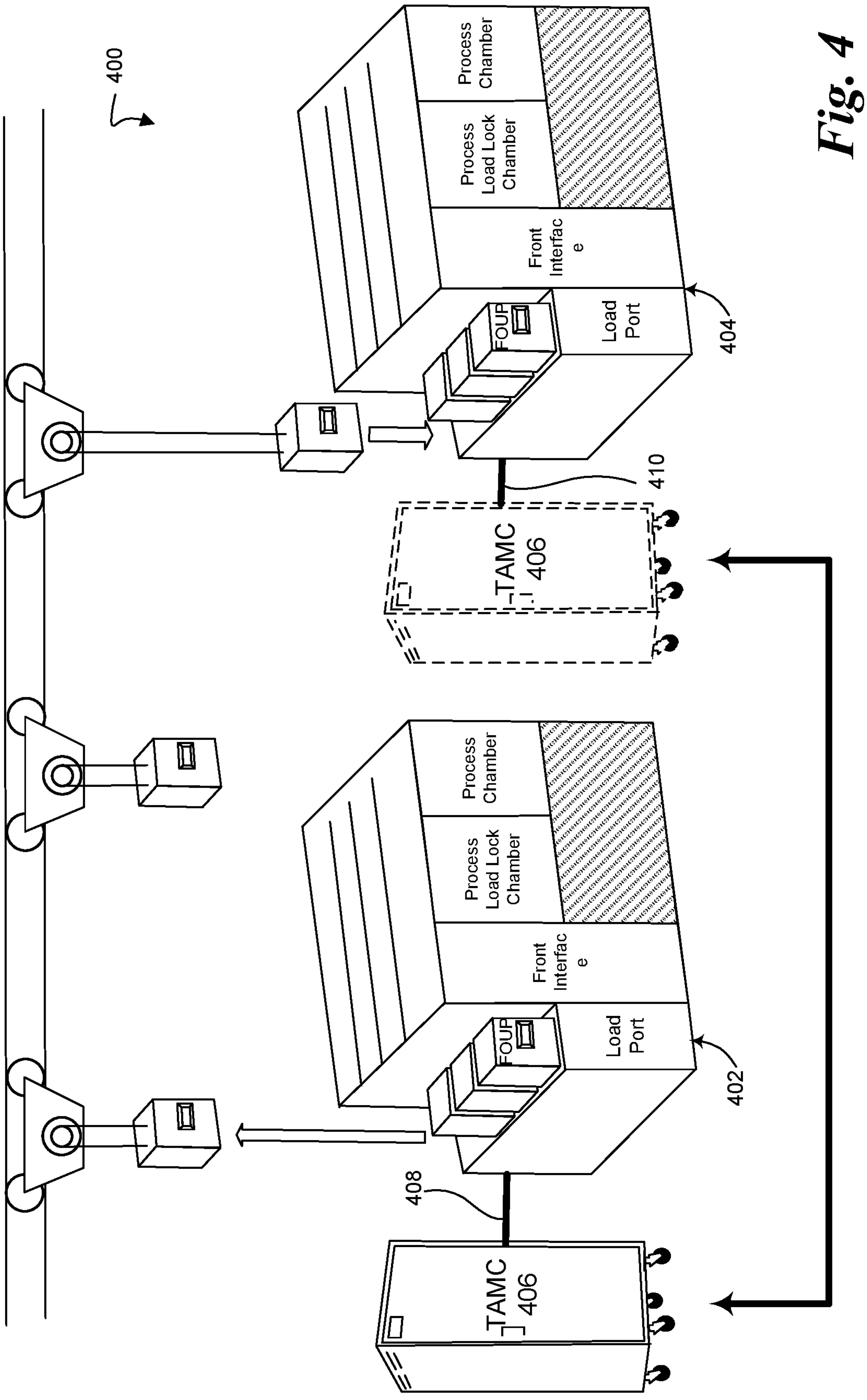
FIG. 4 is a block diagram of another embodiment of an in-line monitoring application using an embodiment of a TAMC apparatus.

FIG. 4 illustrates an embodiment of an in-line monitoring system 400 that uses an embodiment of a TAMC apparatus such as TAMC 300. In monitoring system 400, one or more process equipment modules are positioned in a manufacturing facility. The illustrated embodiment has two process equipment modules 402 and 404, but other embodiments can include more or less process equipment modules than shown. A transport system moves movable carriers, FOUPs in this embodiment, from one process equipment module to the other.

Process equipment module 402 has a sampling tube bus 408 coupled to one or more of its chambers, and process equipment module 404 similarly has a sampling tube bus 410 coupled to one or more of its chambers. Sampling tube buses 408 and 410 are shown in a simplified form to avoid cluttering the drawing, but in an embodiment sampling tube buses 408 and 410 can each include a set of individual sampling tubes and tube buses fluidly coupled to process equipment module 402 as shown in FIG. 2.

TAMC 406 is movable and can be quickly connected and disconnected from sampling tube buses 408 and 410. With the ability to quickly connect and disconnect from tube buses 408 and 410, TAMC 406 can be easily moved between process equipment module 402 and process equipment module 404, for instance by housing it in a rolling cabinet. TAMC apparatus 406 can first be fluidly coupled to process equipment module 402 for a certain period of time to in-line monitor the process equipment cleanliness and also monitor FOUPs that are transferred to it. TAMC system can then be moved and fluidly coupled to process equipment module 404 for subsequent AMC monitoring of its cleanliness and the cleanliness inside FOUPs that are transferred to it.

Figure 5:
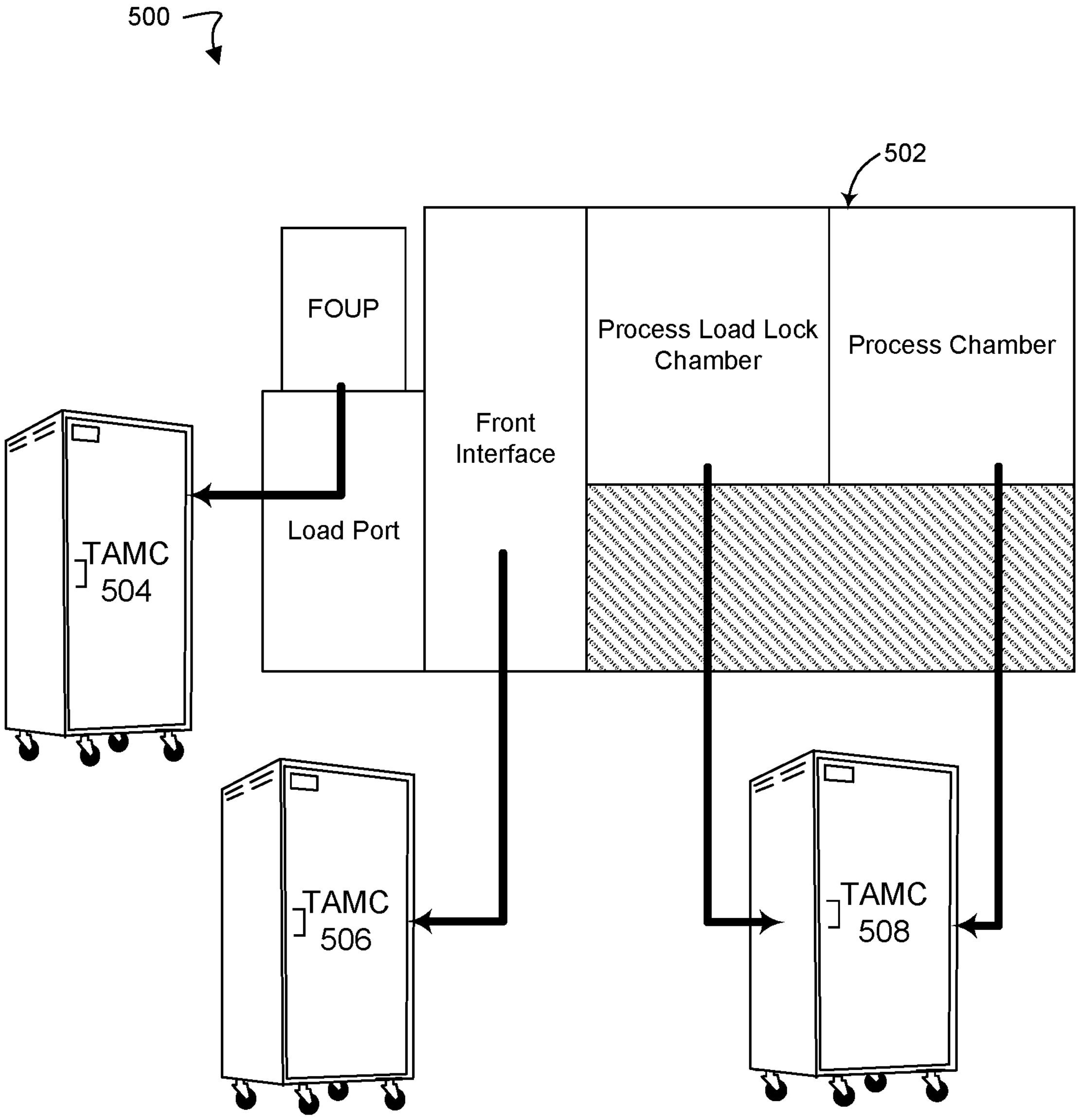
FIG. 5 is a block diagram of another embodiment of an in-line monitoring application using an embodiment of a TAMC apparatus.

FIG. 5 illustrates another embodiment of an in-line monitoring system 500. In system 500, multiple TAMCs can be connected to a process equipment module 502 to focus on independently monitoring specific chambers within the process equipment module.

In the illustrated embodiment, process equipment module 502 has multiple chambers; as before, it has a load port where one or more movable carriers such as a FOUP can be mated, and in the illustrated embodiment it also has a front interface, a process load lock chamber, and a process chamber. Different TAMCs are fluidly coupled to different chambers within process equipment module 502: in the illustrated embodiment one TAMC 504 is fluidly coupled to the load port, another TAMC 506 is fluidly coupled to the front interface, and a third TAMC 508 is fluidly coupled to both the load lock chamber and the process chamber. In other embodiments, the fluid connections can be different than shown. Although not shown in the figure, TAMCs 504-508, as well as process equipment module 502, can be communicatively coupled as shown in FIG. 2, by wire or wirelessly, to each other, to a central server, or both to each other and to a central server.

Figure 6:
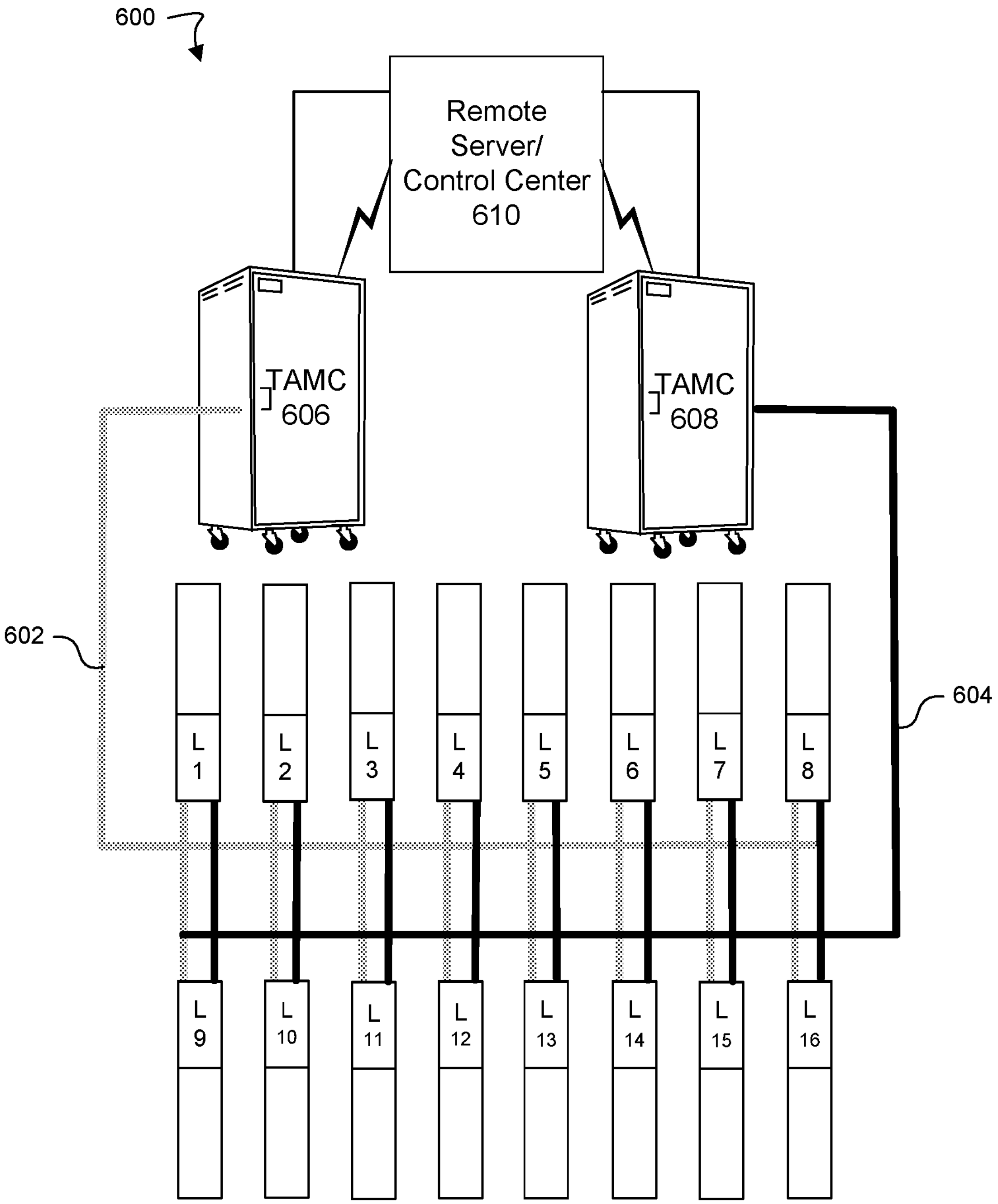
FIG. 6 is a block diagram of another embodiment of an in-line monitoring application using an embodiment of a TAMC apparatus.

FIG. 6 illustrates another embodiment of an in-line monitoring system 600. System 600 includes a plurality of process equipment modules; the illustrated embodiment has 16 process equipment modules labeled L1-L16, but other embodiments can have more or less process equipment modules than shown. The system includes two separate sampling tube buses 602 and 604. Sampling tube bus 602 has one or more individual sampling tubes fluidly coupled to every process equipment module L1-L16, and sampling tube bus 604 also has one or more individual sampling tubes fluidly coupled to every process equipment module L1-L16.

Various sampling tube bus arrangements are possible in different embodiments of system 600. In one embodiment, for instance, sampling tube bus 602 can have all its individual sampling tubes coupled to one type of process equipment module chamber while sampling tube bus 604 can have its individual sampling tubes coupled to another type of chamber. For instance, sampling tube bus 602 can have its individual sampling tubes coupled to the load ports of process equipment modules L1-L16, while sampling tube bus 604 has its individual sampling tubes coupled to the process chambers of process equipment modules L1-L16. In another embodiment, bus 602 can have its individual sampling tubes coupled to one combination of chambers on each process equipment module, while bus 604 has its individual sampling tubes coupled to another combination of chambers in each process equipment module. In still another embodiment, both buses 602 and 604 can have all of their individual sampling tubes coupled to all chambers of every process equipment module, as shown for instance in FIG. 2.

A TAMC is fluidly coupled to each sampling tube bus to collect and analyze samples collected from each individual sampling tube: TAMC 606 is coupled to sampling tube bus 602 and TAMC 608 is fluidly coupled to sampling tube bus 604, so there is a one-to-one correspondence of TAMCs to sampling tube buses. In other embodiments, however, sampling tube buses 602 and 604 could be separated and directed to a greater or lesser number of TAMCs that shown. As in other illustrated embodiments, TAMCs 602-608, as well as individual process equipment modules L1-L16, can be communicatively coupled, by wire or wirelessly, to each other and/or to a central to a remote server/control center 610, as shown in FIG. 2. The communication connection between process equipment modules L1-L16 and server 610 are not shown to avoid cluttering the drawing.

With in-line monitoring system 600, a combination of different in-line TAMC systems may be used to cover the same process region. One or more in-line TAMC system may be fluidly coupled and focused on monitoring the load port FOUP exhaust, while another in-line TAMC system may be fluidly coupled and focused on monitoring FI chamber of all equipment within the targeted process region. Likewise for additional in-line TAMC systems for all load lock chambers and/or process chambers within the targeted process region in the fab.

Figure 7:
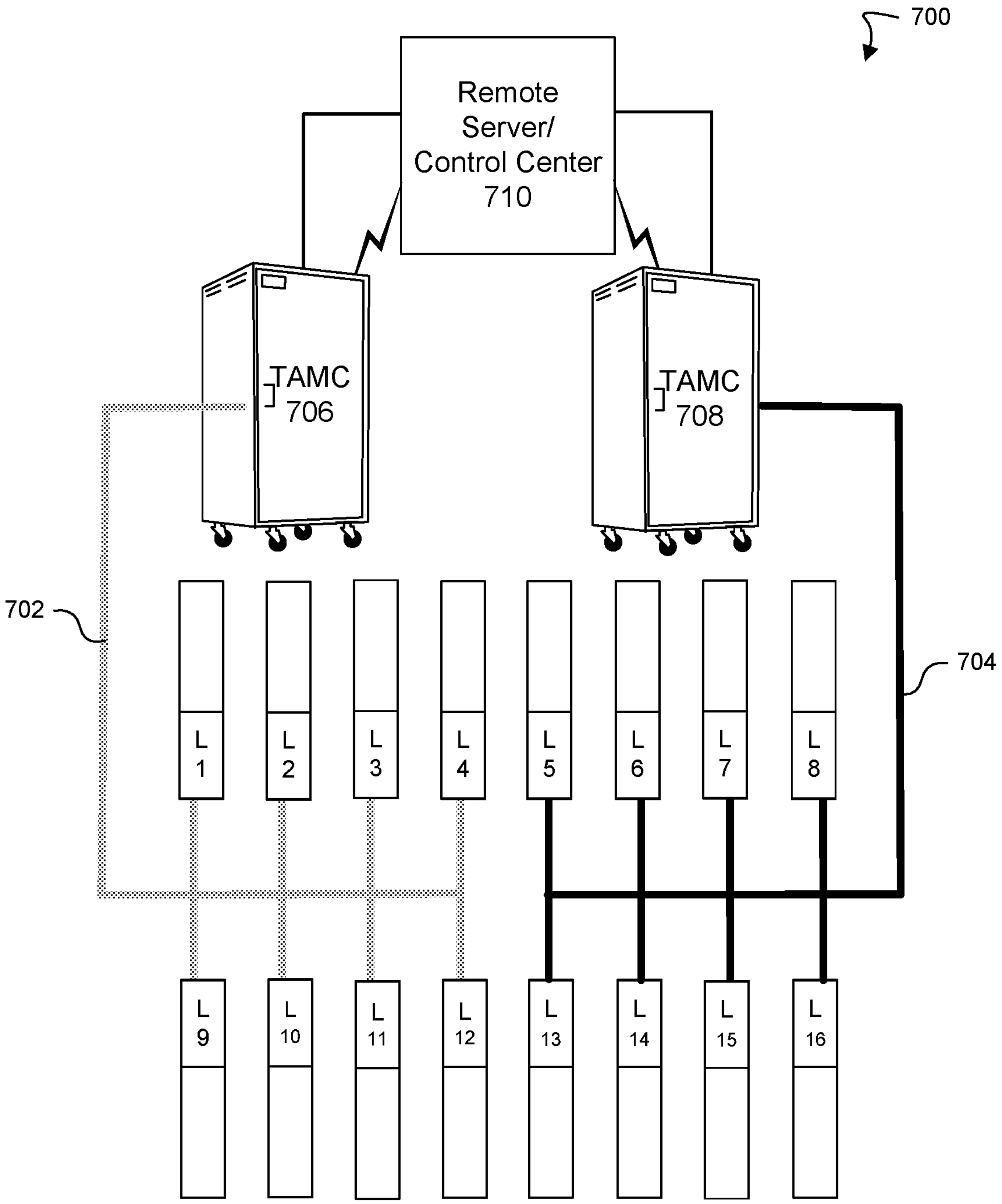
FIG. 7 is a block diagram of another embodiment of an in-line monitoring application using an embodiment of a TAMC apparatus.

FIG. 7 illustrates another embodiment of an in-line monitoring system 700. System 700 includes a plurality of process equipment modules; the illustrated embodiment has 16 process equipment modules labeled L1-L16, but other embodiments can have more or less process equipment modules than shown. The system includes two separate sampling tube buses 702 and 704. Sampling tube bus 702 has one or more individual sampling tubes fluidly coupled to chambers of a subset of the process equipment modules—modules L1-L4 and L9-L12 in this embodiment—and sampling tube bus 704 also has one or more individual sampling tubes fluidly coupled to the chambers of a different subset of process equipment modules—L5-L8 and L13-L16 in this embodiment.

Various sampling tube bus arrangements are possible in different embodiments of system 700. In one embodiment, for instance, sampling tube bus 702 can have all its individual sampling tubes coupled to one type of process equipment module chamber while sampling tube bus 704 can have its individual sampling tubes coupled to another type of chamber. For instance, sampling tube bus 702 can have its individual sampling tubes coupled to the load ports of process equipment modules L1-L4 and L9-L12, while sampling tube bus 704 has its individual sampling tubes coupled to the process chambers of process equipment modules L5-L8 and L13-L16. In another embodiment, bus 702 can have its individual sampling tubes coupled to one combination of chambers on each process equipment module in its subset, while bus 704 has its individual sampling tubes coupled to another combination of chambers in each process equipment module in its subset. In still another embodiment, both buses 702 and 704 can have all of their individual sampling tubes coupled to all chambers of every process equipment module in their subset, as shown for instance in FIG. 2.

A TAMC is fluidly coupled to each sampling tube bus to collect and analyze samples collected from each individual sampling tube: TAMC 706 is coupled to sampling tube bus 702 and TAMC 708 is fluidly coupled to sampling tube bus 704, but in other embodiments sampling tube buses 702 and 704 could be separated and directed to a greater or lesser number of TAMCs that shown. As in other illustrated embodiments, TAMCs 702-708, as well as individual process equipment modules L1-L16, can be communicatively coupled, by wire or wirelessly, to each other and/or to a central to a remote server/control center 710, as shown in FIG. 2. The communication connection between process equipment modules L1-L16 and server 710 are not shown to avoid cluttering the drawing.

With in-line monitoring system 700, TAMCs 706 and 708 can be used and connected to multiple process equipment/modules through expanded manifold design (i.e., more sampling channels) to cover certain process region inside the manufacturing facility. Each in-line TAMC can be configured to monitor the FOUP load port exhaust, FI, load lock, or process chamber) for specific amount of process equipment (and FOUPs).

Figure 8:
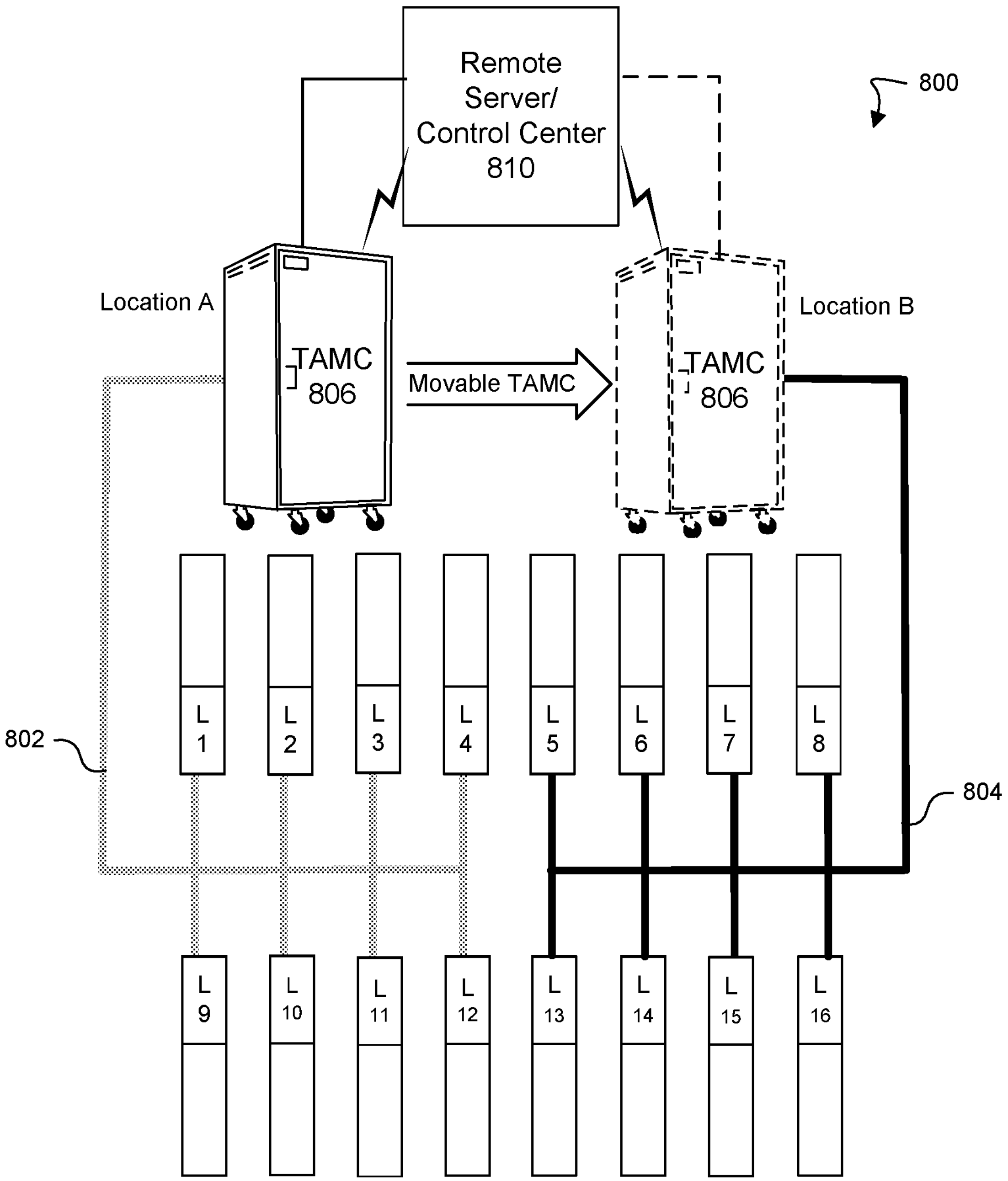
FIG. 8 is a block diagram of another embodiment of an in-line monitoring application using an embodiment of a TAMC apparatus.

FIG. 8 illustrates another embodiment of an in-line monitoring system 800. System 800 includes a plurality of process equipment modules; the illustrated embodiment has 16 process equipment modules labeled L1-L16, but other embodiments can have more or less process equipment modules than shown. The system includes two separate sampling tube buses 802 and 804. Sampling tube bus 802 has one or more individual sampling tubes fluidly coupled to chambers of a subset of the process equipment modules—modules L1-L4 and L9-L12 in this embodiment—and sampling tube bus 804 also has one or more individual sampling tubes fluidly coupled to the chambers of a different subset of process equipment modules—L5-L8 and L13-L16 in this embodiment.

Various sampling tube bus arrangements are possible in different embodiments of system 800. In one embodiment, for instance, sampling tube bus 802 can have all its individual sampling tubes coupled to one type of process equipment module chamber while sampling tube bus 804 can have its individual sampling tubes coupled to another type of chamber. For instance, sampling tube bus 802 can have its individual sampling tubes coupled to the load ports of process equipment modules L1-L4 and L9-L12, while sampling tube bus 804 has its individual sampling tubes coupled to the process chambers of process equipment modules L5-L8 and L13-L16. In another embodiment, bus 802 can have its individual sampling tubes coupled to one combination of chambers on each process equipment module in its subset, while bus 804 has its individual sampling tubes coupled to another combination of chambers in each process equipment module in its subset. In still another embodiment, both buses 802 and 804 can have all of their individual sampling tubes coupled to all chambers of every process equipment module in their subset, as shown for instance in FIG. 2.

In the illustrated embodiment, a movable TAMC 806 is fluidly coupled to each sampling tube bus at a different time to collect and analyze samples collected from each individual sampling tube in that bus. With the ability to quickly connect and disconnect from sampling tube buses 802 and 804, TAMC 806 can be easily moved between sampling tube buses, for instance by housing it in a rolling cabinet. TAMC 806 is first coupled to sampling tube bus 802. When finished monitoring that corresponding subset of process equipment modules, TAMC 806 is then uncoupled from sampling tube bus 802 and fluidly coupled to sampling tube bus 804. As in other illustrated embodiments, TAMC 806, as well as individual process equipment modules L1-L16, can be communicatively coupled, by wire or wirelessly, to each other and/or to a central to a remote server/control center 810, as shown in FIG. 2. The communication connection between process equipment modules L1-L16 and server 810 are not shown to avoid cluttering the drawing.

With in-line monitoring system 800, the single inline TAMC system is connected to multiple process equipment/modules through expanded manifold design (more sampling channels) to cover certain process region inside the manufacturing facility. In-line TAMC may be moved from location A to location B covering AMC monitoring in location B region with multiple process equipment. In another embodiment, the single in-line TAMC system connected to multiple process equipment/modules through expanded manifold design (more sampling channels) to cover certain process region inside the manufacturing facility can be movable. The in-line TAMC may be moved from location A to location B covering AMC monitoring in location B region with multiple process equipment.

Figure 9:
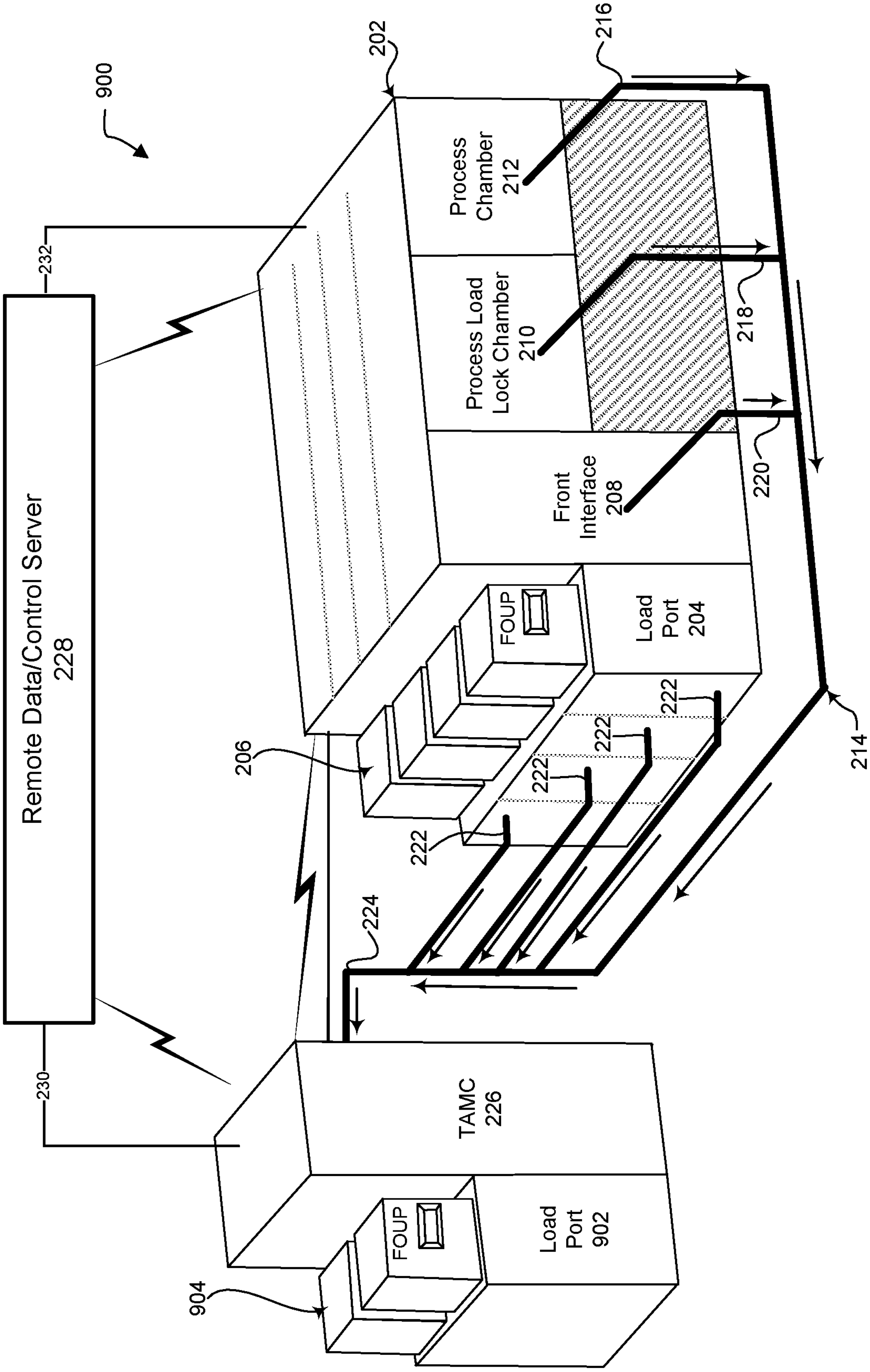
FIG. 9 is a block diagram of another embodiment of an in-line monitoring application using an embodiment of a TAMC apparatus.

FIG. 9 illustrates another embodiment of an in-line monitoring system 900. Monitoring system 900 is in most respects similar to monitoring system 200 shown in FIG. 2: the fluid couplings between TAMC 226 and the different chambers of process equipment module as substantially 202 are substantially the same, and the communicative couplings between TAMC 226, process equipment module 202, and remote data/control server 228 are also substantially the same.

The primary difference between system 900 and system 200 is that in system 900 TAMC 226 includes its own load port 902 to which movable carriers 904 can be mated for analysis, just as movable carriers can be mated to load port 204 of process equipment module 202. In one embodiment, load port 902 provides additional locations where movable carriers 904 and 206 can be docked for analysis. In another embodiment, load port 902 allows TAMC 226 to serve as a base station for purpose-specific movable carriers 904. For example, a movable carrier 904 can be a special process health monitoring FOUP that carries battery-powered sensors or sampling collectors inside the FOUP (instead of the semiconductor wafers it would normally carry) to perform further detailed TAMC analysis, FOUP cleaning, or in-FOUP battery charging. Purpose-specific movable carriers/FOUPs can also be transferred to load port 204, the same as a regular process FOUP. Load port 902 can also be used to perform AMC analysis directly on the standard movable carriers or process FOUPs, with or without wafers inside.

The above description of embodiments, including what is described in the abstract, is not intended to be exhaustive or to limit the invention to the described forms. Specific embodiments of, and examples for, the invention are described herein for illustrative purposes, but various equivalent modifications are possible within the scope of the invention in light of the above detailed description, as those skilled in the relevant art will recognize. In-line TAMC system with load port design for direct FOUP docking and analysis.

The terms used in the following claims should not be interpreted to limit the invention to the specific embodiments disclosed in the specification and the claims. Rather, the scope of the invention is to be determined entirely by the following claims, which are to be interpreted using established claim interpretation doctrines.

What is claimed is:

1. An airborne molecular contamination (AMC) monitoring apparatus comprising:

a manifold including:

an inlet tube that reduces or eliminates dead space, a buffer tank fluidly coupled by a multi-way valve to the inlet tube, and a plurality of outlets fluidly coupled to the buffer tank;

a sampling tube bus fluidly coupled to the inlet tube, the sampling tube bus comprising a plurality of individual sampling tubes, each individual sampling tube being fluidly coupled to the inlet tube of the manifold by a multi-way valve;

two or more analyzers, each fluidly coupled by a valve to a corresponding one of the plurality of outlets of the manifold to analyze the composition of fluid drawn into the manifold through one or more of the plurality of individual sampling tubes;

a pump fluidly coupled in the manifold upstream of the buffer tank, wherein the pump draws a sample into at least one of the plurality of individual sampling tubes; and a control and communication system coupled to the two or more analyzers.

2. The AMC monitoring apparatus of claim 1 wherein each individual sampling tube is coupled to a chamber of a process equipment station.

3. The AMC monitoring apparatus of claim 1 wherein the each of the two or more analyzers can include an individual or total volatile organic compounds (VOC) detector, an acid compound detector, a base compound detector, a sulfide compound detector, an amine compound detector, an air particle or aerosol count detector, a humidity detector, a temperature detector, a chemical coolant detector, an anion detector, a cation detector, a metal ion detector, or a doping ion detector.

4. The AMC monitoring apparatus of claim 1 wherein the manifold further comprises:

a clean air inflow and a clean air outflow coupled to the buffer tank to flush out the interior of the buffer tank.

5. The AMC monitoring apparatus of claim 4 wherein the pump is fluidly coupled to the interior of the buffer tank.

6. The AMC monitoring apparatus of claim 5, further comprising one or more analyzers coupled to the inlet tube upstream of the multi-way valve that couples the one or more outlets of the inlet tube to the buffer tank.

7. The AMC monitoring apparatus of claim 6 wherein the one or more analyzers coupled to the inlet tube upstream of the multi-way valve include a temperature analyzer or a humidity analyzer.

8. The AMC monitoring apparatus of claim 1 wherein the control and communication system is communicatively coupled, wirelessly or by wire, to a remote server, to a process equipment module, or to both a remote server and a process equipment module.

9. The AMC monitoring apparatus of claim 1, further comprising a load port attached to the AMC monitoring apparatus and fluidly coupled to at least one individual sampling tube.

10. The AMC monitoring apparatus of claim 1 wherein each multi-way valve can be selectively set to direct a sample into the inlet tube or set to vent the sample without directing it into the one or more sampling tubes.

11. An environmental monitoring system comprising:

a sampling bus comprising a plurality of sampling tubes, wherein each sampling tube is fluidly coupled to one or more chambers of at least one process equipment module;

one or more airborne molecular contamination (AMC) apparatuses fluidly coupled to the sampling bus, each airborne contamination apparatuses comprising:

a manifold including:

an inlet tube that reduces or eliminates dead space, a buffer tank fluidly coupled by a multi-way valve to the inlet tube, and a plurality of outlets fluidly coupled to the buffer tank;

a sampling tube bus fluidly coupled to the inlet tube, the sampling tube bus comprising a plurality of individual sampling tubes, each individual sampling tube being fluidly coupled to the inlet tube of the manifold by a multi-way valve, two or more analyzers, each fluidly coupled by a valve to a corresponding one of the plurality of outlets of the manifold to analyze the composition of fluid drawn into the manifold through one or more of the plurality of individual sampling tubes, a pump fluidly coupled in the manifold upstream of the buffer tank, wherein the pump draws a sample into at least one of the plurality of individual sampling tubes, and a control and communication system coupled to the two or more analyzers; and a remote server communicatively coupled, wirelessly or by wire, to the control and communication system.

12. The system of claim 11 wherein each process equipment module includes a load port to receive a moveable carrier carrying items being manufactured.

13. The system of claim 12 wherein at least one individual sampling tube is fluidly coupled to each load port to sample the environment inside the movable carrier when the movable carrier is placed on the load port.

14. The system of claim 12 wherein individual sampling tubes are fluidly coupled to an interface chamber, a lock load chamber, and a process chamber of the process equipment module to sample the environment within each chamber.

15. The system of claim 11 wherein the at least one process equipment module comprises a plurality of process equipment modules grouped into two or more sets, each set having its own sampling bus and its own AMC apparatus coupled to the sampling bus.

16. The system of claim 11 wherein the at least one process equipment module comprises a plurality of process equipment modules grouped into two or more sets, each set having its own sampling bus, and wherein a single movable AMC apparatus is connected and disconnected from each sampling bus to monitor each set.

17. The system of claim 11 wherein the at least one process equipment module comprises a plurality of process equipment modules, wherein each process equipment module is coupled to a pair of sampling buses and wherein each of the pair of sampling buses is connected to its own environmental monitoring apparatus.

18. The system of claim 11 wherein the control and communication system is communicatively coupled, wirelessly or by wire, to a remote server, to the at least one process equipment module, or to both the remote server and the at least one process equipment module.

19. The system of claim 11, further comprising a load port attached to at least one of the one or more AMC apparatuses and fluidly coupled to at least one individual sampling tube of the AMC apparatus to which it is attached.

20. The system of claim 11 wherein each multi-way valve can be selectively set to direct a sample into the inlet tube or set to vent the sample without directing it into the one or more sampling tubes.

* * * * *